United States Patent
Bernhardt et al.

(10) Patent No.: US 9,323,887 B2
(45) Date of Patent: *Apr. 26, 2016

(54) DEVICE AND COMPUTED TOMOGRAPHY SCANNER FOR DETERMINING AND VISUALIZING THE PERFUSION OF THE MYOCARDIAL MUSCLE

(71) Applicant: Siemens Aktiengesellschaft, Munich (DE)

(72) Inventors: Dominik Bernhardt, Hausen (DE); Michael Scheuering, Nuernberg (DE); Fernando Vega-Higuera, Erlangen (DE)

(73) Assignee: SIEMENS AKTIENGESELLSCHAFT, Munich (DE)

( * ) Notice: Subject to any disclaimer, the term of this patent is extended or adjusted under 35 U.S.C. 154(b) by 0 days.

This patent is subject to a terminal disclaimer.

(21) Appl. No.: 14/664,075

(22) Filed: Mar. 20, 2015

(65) Prior Publication Data

US 2015/0193574 A1  Jul. 9, 2015

Related U.S. Application Data

(63) Continuation of application No. 14/307,544, filed on Jun. 18, 2014, now Pat. No. 9,002,091, which is a continuation of application No. 13/293,172, filed on Nov. 10, 2011, now Pat. No. 8,831,320.

(30) Foreign Application Priority Data

Nov. 12, 2010 (DE) .......................... 10 2010 043 849

(51) Int. Cl.
*G06K 9/00* (2006.01)
*G06F 19/12* (2011.01)
(Continued)

(52) U.S. Cl.
CPC . *G06F 19/12* (2013.01); *A61B 6/03* (2013.01); *A61B 6/032* (2013.01); *A61B 6/481* (2013.01);
(Continued)

(58) Field of Classification Search
None
See application file for complete search history.

(56) References Cited

U.S. PATENT DOCUMENTS

| 7,285,095 B2 | 10/2007 | Ito et al. |
| 8,045,773 B2 | 10/2011 | Lautenschlager |

(Continued)

FOREIGN PATENT DOCUMENTS

DE   102007029886 A1   1/2009

OTHER PUBLICATIONS

Kenneth A. Miles and M. R. Griffiths; Perfusion CT: a worthwhile enhancement? The British Journal of Radiology, Apr. 2003,pp. 220-231; Magazine; 2003.

(Continued)

*Primary Examiner* — Shefali Goradia
(74) *Attorney, Agent, or Firm* — Harness, Dickey & Pierce, P.L.C.

(57) ABSTRACT

A device is disclosed for determining and visualizing the perfusion of the myocardial muscle with the aid of static CCTA images. In at least one embodiment, the device includes a segmentation unit for segmenting the coronary blood vessels and the left myocardial muscle from a CCTA image of the heart; a first simulation unit for simulating the blood flow through the coronary blood vessels; and a second simulation unit by which the local perfusion of the myocardial muscle is determined on the basis of the ascertained blood flow into different regions of the myocardial muscle. The perfusion of the different regions of the myocardial muscle is visualized in a schematized image on a visualization unit. By virtue of the proposed device it is possible to dispense with further imaging examinations after the performance of a CCTA scan, thereby relieving the pressure both on the part of the physician and on the part of the patient.

20 Claims, 2 Drawing Sheets

(51) Int. Cl.

| | | |
|---|---|---|
| *A61B 6/03* | (2006.01) | |
| *A61B 6/00* | (2006.01) | |
| *G06T 7/00* | (2006.01) | |
| *G06F 19/00* | (2011.01) | |
| *G06F 17/18* | (2006.01) | |

(52) U.S. Cl.
CPC .............. *A61B 6/503* (2013.01); *A61B 6/504* (2013.01); *A61B 6/507* (2013.01); *G06F 17/18* (2013.01); *G06F 19/3437* (2013.01); *G06T 7/0012* (2013.01); *G06T 2207/10076* (2013.01); *G06T 2207/10081* (2013.01); *G06T 2207/30048* (2013.01); *G06T 2207/30104* (2013.01)

(56) References Cited

U.S. PATENT DOCUMENTS

| | | | |
|---|---|---|---|
| 8,150,128 | B2 | 4/2012 | Konofagou et al. |
| 8,150,490 | B2 | 4/2012 | Groth et al. |
| 8,311,791 | B1 | 11/2012 | Avisar |
| 8,386,188 | B2 | 2/2013 | Taylor et al. |
| 2004/0138864 | A1 | 7/2004 | Kurzweil et al. |
| 2005/0059876 | A1 | 3/2005 | Krishnan et al. |
| 2006/0104516 | A1 | 5/2006 | Lee et al. |
| 2009/0003680 | A1 | 1/2009 | Lautenschlager |

OTHER PUBLICATIONS

Gülsün and Tek: "Robust Vessel Tree Modeling", Medical Image Computing and Computer Assisted Intervention—MICCAI 2008, vol. 5241/2008, pp. 602-611; Others.

Zheng, Y. et al., "Four-Chamber Heart Modeling and Automatic Segmentation for 3D Cardiac CT Volumes Using Marginal Space Learning and Steerable Features", IEEE Trans. Medical Imaging (2008) 27(11), pp. 1668-1681; Others; 2008.

N. Arslan et al., CFD Modelling of Blood Flow Inside Human Left Coronary Artery Bifurcation with Aneurysms, 3rd European Medical and Biological Engineering Conference, Nov. 20-25, 2005, pp. 357-363, Prag; Others.

R. Begum et al., Lattice Boltzmann Method and its Applications to Fluid Flow Problems, European Journal of Scientific Research, vol. 22, No. 2 (2008), pp. 216-231; Others.

German Office Action dated Jun. 24, 2011 for German Application No. DE 10 2010 043 849.9.

Certified German Priority document for German Application No. DE 10 2010 043 849.9 filed Nov. 12, 2010.

Spreeuwers, Luuk, and Marcel Breeuwer. Automatic detection of myocardial boundaries in MR cardio perfusion images Medical Image Computing and Computer-Assisted Intervention-MICCAI 2001. Springer Berlin Heidelberg, 2001.

Chinese Office Action and English translation thereof dated Apr. 4, 2014.

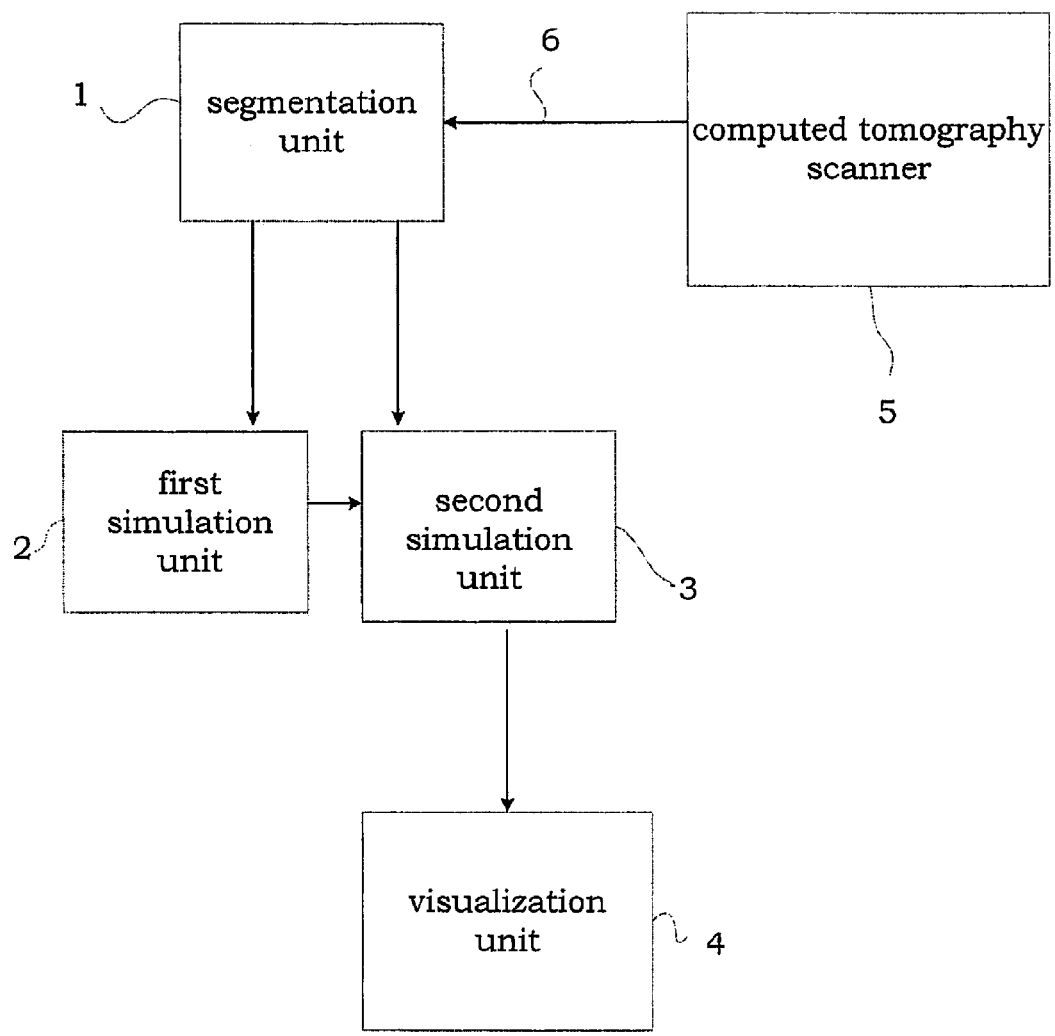

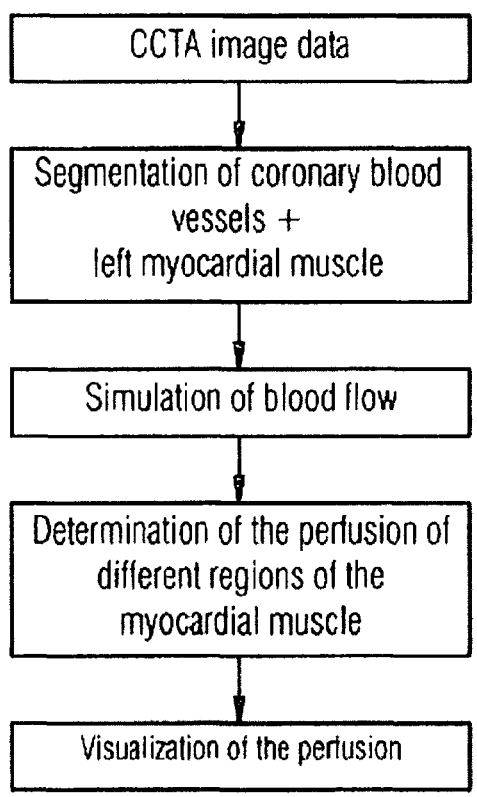

DEVICE AND COMPUTED TOMOGRAPHY SCANNER FOR DETERMINING AND VISUALIZING THE PERFUSION OF THE MYOCARDIAL MUSCLE

PRIORITY STATEMENT

This application is a continuation application of and claims priority under 35 U.S.C. §120/121 to U.S. application Ser. No. 14/307,544 filed Jun. 18, 2014, which is a continuation of U.S. Ser. No. 13/293,172 filed Nov. 10, 2011, which claims priority under 35 U.S.C. §119 to German patent application number DE 10 2010 043 849.9 filed Nov. 12, 2010, the entire contents of each of which are hereby incorporated herein by reference.

FIELD

At least one embodiment of the present invention generally relates to a device for determining and visualizing the perfusion of the myocardial muscle with the aid of non-dynamic computed tomographic angiography.

BACKGROUND

Multilayer computed tomography or multi-slice CT (MSCT) is frequently employed nowadays for investigating heart disease. Typically this entails performing a single CT scan by means of coronary CT angiography (CCTA) in order to obtain image information about the coronary anatomy and potential pathologies. In the event of a stenosis of the coronary blood vessels that is detectable in the images, the implications of said lesion for the myocardial muscle must be investigated. Different techniques for measuring the blood flow through the myocardial muscle are applied for this purpose. Examples include nuclear imaging, magnetic resonance tomography or dynamic perfusion measurement by means of computed tomography. An example of performing dynamic perfusion measurement by means of computed tomography is described in K. A. Miles et al., "Perfusion CT: a worthwhile enhancement?", Br. J. Radiol. 2003, 76 (904), pages 220 to 231.

However, these techniques lead to an additional load being imposed on the patient and the treating physician. The physician must employ a more complex technique than that of a single CCTA scan. The patient must undergo an additional time-consuming examination and in the case of nuclear imaging or computed tomography is exposed to additional ionizing radiation.

DE 10 2007 029 886 A1 describes a method for segmenting a myocardial muscle wall as well as a device for detecting a pathologically changed coronary artery. With the method and the device, the myocardial muscle is segmented and the myocardial muscle wall visualized in order to provide enhanced visualization of the pumping function of the heart. In this case the segmented myocardial muscle wall is divided into sections to which the coronary arteries can be assigned. This visualization can then provide pointers to the perfusion of the myocardial muscle wall and identify the affected coronary artery in order then to subject the latter to a more precise and thorough examination.

SUMMARY

In at least one embodiment of the present invention, a device and a computed tomography scanner are disclosed for determining and visualizing the perfusion of the myocardial muscle in computed tomographic angiography which enable a lessening of the load both for the patient and for the physician.

A device and a computed tomography scanner are disclosed. Advantageous embodiments of the device are the subject matter of the dependent claims or can be derived from the following description and the example embodiment.

The proposed device of at least one embodiment for determining and visualizing the perfusion of the myocardial muscle includes at least a segmentation unit, a first simulation unit, a second simulation unit and a visualization unit. The segmentation unit is embodied so as to segment coronary blood vessels and the left myocardial muscle from a CCTA image of the heart. The first simulation unit is embodied for the purpose of simulating a blood flow through the coronary blood vessels on the basis of the segmented coronary blood vessels and determine therefrom the blood flow into different regions of the segmented myocardial muscle into which different branches of the coronary blood vessels lead.

In at least one embodiment, a subdivision of the myocardial muscle into different regions which are supplied by the respective branches is accordingly carried out on the basis of the different segmented branches of the coronary blood vessels. The second simulation unit is embodied such that it simulates the local perfusion of the myocardial muscle for the different regions on the basis of the determined blood flow into the different regions of the myocardial muscle and of the segmented myocardial muscle. This simulation can take into account a different load on the patient, i.e. different high blood flows into the heart, in order to detect the perfusion of the myocardial muscle in different stress situations of the patient. The perfusion of the myocardial muscle based on the model used in the second simulation unit is then visualized on a preferably schematized image of the myocardial muscle. This can of course be realized in different ways, e.g. by specification of average perfusion values in the different regions in each case or by colored marking of the different regions, the color then providing a pointer to the nature of the perfusion, e.g. good perfusion in green, slightly reduced perfusion in yellow, and poor perfusion in red.

The device of at least one embodiment may already be part of a computed tomography scanner or be connected to a computed tomography scanner. The device of at least one embodiment can be implemented e.g. in the form of a software module on a computer system and/or a control and/or evaluation system of the computed tomography scanner.

BRIEF DESCRIPTION OF THE DRAWINGS

The device is explained briefly once again below with reference to an example embodiment taken in conjunction with the drawings, in which:

FIG. 1 shows a schematic representation of an embodiment of the device, and

FIG. 2 shows a schematic workflow of individual processes executing in an embodiment of the device.

DETAILED DESCRIPTION OF THE EXAMPLE EMBODIMENTS

Various example embodiments will now be described more fully with reference to the accompanying drawings in which only some example embodiments are shown. Specific structural and functional details disclosed herein are merely representative for purposes of describing example embodiments. The present invention, however, may be embodied in many alternate forms and should not be construed as limited to only the example embodiments set forth herein.

Accordingly, while example embodiments of the invention are capable of various modifications and alternative forms, embodiments thereof are shown by way of example in the drawings and will herein be described in detail. It should be understood, however, that there is no intent to limit example embodiments of the present invention to the particular forms disclosed. On the contrary, example embodiments are to cover all modifications, equivalents, and alternatives falling within the scope of the invention. Like numbers refer to like elements throughout the description of the figures.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items.

It will be understood that when an element is referred to as being "connected," or "coupled," to another element, it can be directly connected or coupled to the other element or intervening elements may be present. In contrast, when an element is referred to as being "directly connected," or "directly coupled," to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

To that end, FIG. 1 shows in greatly schematized form an example embodiment of the device which is composed of at least a segmentation unit 1, a first simulation unit 2 for simulating the blood flow, a second simulation unit 3 for determining the perfusion of the myocardial muscle, and a visualization unit 4 for visualizing the perfusion. The device is connected to a computed tomography scanner 5 by way of which the image data 6 of a CCTA of the heart of a patient is transmitted. The image data 6 is processed in the segmentation unit 1 in order to segment the coronary blood vessels and the left myocardial muscle. This workflow is shown by way of example in FIG. 2. On the basis of the segmented image data the blood flow through the coronary blood vessels is then simulated in the first simulation unit 2 in order to determine therefrom the blood flow into different regions of the myocardial muscle that are supplied by the individual branches of the coronary blood vessels. With the aid of this local blood inflow the perfusion of the different regions of the segmented myocardial muscle is then determined in the second simulation unit 3. The result is presented on a screen by way of the visualization unit 4.

The device of an embodiment for determining and visualizing the perfusion of the myocardial muscle includes at least a segmentation unit, a first simulation unit, a second simulation unit and a visualization unit. The segmentation unit is embodied so as to segment coronary blood vessels and the left myocardial muscle from a CCTA image of the heart. The first simulation unit is embodied for the purpose of simulating a blood flow through the coronary blood vessels on the basis of the segmented coronary blood vessels and determine therefrom the blood flow into different regions of the segmented myocardial muscle into which different branches of the coronary blood vessels lead.

In an embodiment, a subdivision of the myocardial muscle into different regions which are supplied by the respective branches is accordingly carried out on the basis of the different segmented branches of the coronary blood vessels. The second simulation unit is embodied such that it simulates the local perfusion of the myocardial muscle for the different regions on the basis of the determined blood flow into the different regions of the myocardial muscle and of the segmented myocardial muscle. This simulation can take into account a different load on the patient, i.e. different high blood flows into the heart, in order to detect the perfusion of the myocardial muscle in different stress situations of the patient. The perfusion of the myocardial muscle based on the model used in the second simulation unit is then visualized on a preferably schematized image of the myocardial muscle. This can of course be realized in different ways, e.g. by specification of average perfusion values in the different regions in each case or by colored marking of the different regions, the color then providing a pointer to the nature of the perfusion, e.g. good perfusion in green, slightly reduced perfusion in yellow, and poor perfusion in red.

The device of an embodiment therefore uses an existing static CCTA image in order to simulate the blood flow through the coronary blood vessels and to estimate or predict the perfusion of the myocardial muscle with the aid of a perfusion model on the basis of the simulated blood flow.

By virtue of the device of an embodiment, it is no longer necessary to conduct any other imaging examination if stenoses are identifiable in the CCTA image. The device therefore reduces the load and stress for the patient and the time and effort involved on the part of the treating physician. An additional dynamic CT scan for perfusion measurement, along with the exposure to radiation associated therewith, or other examinations are no longer necessary for this purpose.

In an embodiment of the device, the first simulation unit is embodied such that it generates a model of the coronary blood vessels and of the myocardial muscle from the segmented coronary blood vessels and the segmented left myocardial muscle and performs the simulation of the blood flow with the aid of the model. In another embodiment, the simulation can also be performed directly on the basis of the segmented voxels, in particular using the so-called lattice Boltzmann method (LBM). An example of automatic segmentation of the ventricles of the heart can be found in Y. Zheng et al., "Four-chamber heart modeling and automatic segmentation for 3-D cardiac CT volumes using marginal space learning and steerable features", IEEE Trans. Med. Imaging 2008, 27(11), pages 1668 to 1681, in respect of the automatic segmentation of the coronary tree in M. A. Gülsün et al., "Robust Vessel Tree Modeling", in Medical Image Computing and Computer Assisted Intervention—MICCAI 2008, Volume 5241/2008, pages 602 to 611. Examples for the simulation of the blood flow can be found in N. Arslan et al., "CFD Modelling of Blood Flow Inside Human Left Coronary Artery Bifurcation with Aneurysms", 3rd European Medical and Biomedical Engineering Conference, November pp. 20-25, 2005, Prague, or in R. Begum et al., "Lattice Boltzmann Method and its Applications to Fluid Flow Problems", European Journal of Scientific Research, Vol. 22, No. 2 (2008), pages 216 to 231. The entire contents of each of the aforementioned documents are hereby incorporated herein by reference. These techniques can also be employed in the first simulation unit of the device of an embodiment.

In an embodiment, the first simulation unit is embodied such that it uses a statistical model in order to determine time functions for the arterial inflow and venous outflow from the CCTA image on the basis of the accumulation of contrast agent in the coronary blood vessels and the left myocardial muscle. The simulation of the blood flow in the coronary blood vessels is then performed using these values. Preferably reference is made in addition to the injection protocol used in the case of the corresponding patient when the contrast agent was injected for the purpose of generating the CCTA image. The injection protocol is normally chosen specifically for the particular patient and therefore already contains information that can be used for determining the time functions.

The perfusion model used in the second simulation unit preferably simulates firstly the dynamic accumulation of contrast agent in the myocardial muscle under the predefined boundary conditions, i.e. the simulated blood inflow into the different regions and the size of the regions that is evident from the segmented data. In this case a reduced blood flow into the different regions through the corresponding branches of the coronary blood vessels extending into the regions manifests itself in the different contrast agent accumulation. The result is comparable with the result of a dynamic CT angiography that has actually been performed. In a subsequent step the desired perfusion data can then be calculated on the basis of this result using known techniques, such as e.g. the blood volume in ml/100 ml (tissue)/min or the maximum blood volume in ml/100 ml (tissue), for the different regions in each case. The data can be visualized e.g. with the aid of what is called a polar map (17-segment model) on a monitor screen.

The device of an embodiment may already be part of a computed tomography scanner or be connected to a computed tomography scanner. The device of an embodiment can be implemented e.g. in the form of a software module on a computer system and/or a control and/or evaluation system of the computed tomography scanner.

The patent claims filed with the application are formulation proposals without prejudice for obtaining more extensive patent protection. The applicant reserves the right to claim even further combinations of features previously disclosed only in the description and/or drawings.

The example embodiment or each example embodiment should not be understood as a restriction of the invention. Rather, numerous variations and modifications are possible in the context of the present disclosure, in particular those variants and combinations which can be inferred by the person skilled in the art with regard to achieving the object for example by combination or modification of individual features or elements or method steps that are described in connection with the general or specific part of the description and are contained in the claims and/or the drawings, and, by way of combinable features, lead to a new subject matter or to new method steps or sequences of method steps, including insofar as they concern production, testing and operating methods.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

Further, elements and/or features of different example embodiments may be combined with each other and/or substituted for each other within the scope of this disclosure and appended claims.

Still further, any one of the above-described and other example features of the present invention may be embodied in the form of an apparatus, method, system, computer program, tangible computer readable medium and tangible computer program product. For example, of the aforementioned methods may be embodied in the form of a system or device, including, but not limited to, any of the structure for performing the methodology illustrated in the drawings.

Even further, any of the aforementioned methods may be embodied in the form of a program. The program may be stored on a tangible computer readable medium and is adapted to perform any one of the aforementioned methods when run on a computer device (a device including a processor). Thus, the tangible storage medium or tangible computer readable medium, is adapted to store information and is adapted to interact with a data processing facility or computer device to execute the program of any of the above mentioned embodiments and/or to perform the method of any of the above mentioned embodiments.

The tangible computer readable medium or tangible storage medium may be a built-in medium installed inside a computer device main body or a removable tangible medium arranged so that it can be separated from the computer device main body. Examples of the built-in tangible medium include, but are not limited to, rewriteable non-volatile memories, such as ROMs and flash memories, and hard disks. Examples of the removable tangible medium include, but are not limited to, optical storage media such as CD-ROMs and DVDs; magneto-optical storage media, such as MOs; magnetism storage media, including but not limited to floppy disks (trademark), cassette tapes, and removable hard disks; media with a built-in rewriteable non-volatile memory, including but not limited to memory cards; and media with a built-in ROM, including but not limited to ROM cassettes; etc. Furthermore, various information regarding stored images, for example, property information, may be stored in any other form, or it may be provided in other ways.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A device for simulating a perfusion of a myocardial muscle comprising:
    a first simulation unit to simulate a blood flow through coronary blood vessels on the basis of segmented coronary blood vessels from a static coronary computed tomography angiography (CCTA) image, and to determine the blood flow into different regions of the myocardial muscle into which different branches of the coronary blood vessels lead; and
    a second simulation unit to simulate a local perfusion of the myocardial muscle for the different regions on the basis of the determined blood flow into the different regions of the myocardial muscle.

2. The device as claimed in claim 1, wherein the first simulation unit is configured to calculate a model of the coronary blood vessels and of the myocardial muscle on the basis of the segmented coronary blood vessels and of a left myocardial muscle and to perform the simulation of the blood flow with the aid of the model.

3. The device as claimed in claim 2, wherein the first simulation unit is configured to use a statistical model to determine time functions for an arterial inflow and a venous outflow from the CCTA image on the basis of an accumulation of a contrast agent in the coronary blood vessels and a left myocardial muscle.

4. The device as claimed in claim 3, wherein the first simulation unit is additionally configured to use data of an injection protocol used for administering the contrast agent for the purpose of determining the time functions.

5. A computed tomography scanner comprising the device as claimed in claim 2.

6. The device as claimed in claim 1, wherein the first simulation unit is configured to simulate the blood flow through the coronary blood vessels on the basis of the segmented coronary blood vessels using a lattice Boltzmann method.

7. The device as claimed in claim 1, wherein the first simulation unit is configured to use a statistical model to determine time functions for an arterial inflow and a venous outflow from the CCTA image on the basis of an accumulation of a contrast agent in the coronary blood vessels and a left myocardial muscle.

8. The device as claimed in claim 7, wherein the first simulation unit is additionally configured to use data of an injection protocol used for administering the contrast agent for the purpose of determining the time functions.

9. The device as claimed in claim 1, wherein the second simulation unit is configured to initially simulate a dynamic accumulation of a contrast agent in the myocardial muscle and then calculate perfusion parameters for the local of the myocardial muscle from the dynamic contrast agent accumulation.

10. A computed tomography scanner comprising the device as claimed in claim 1.

11. The device of claim 1, further comprising:
    a visualization unit to visualize an image of the myocardial muscle from which the local perfusion for the different regions of the myocardial muscle is identifiable.

12. The device of claim 1, wherein the second simulation unit is configured to determine the local perfusion for the different regions based on different loads on a patient.

13. A method for simulating a perfusion of a myocardial muscle, comprising:
    simulating a blood flow through coronary blood vessels of a heart on the basis of segmented coronary blood vessels from a static coronary computed tomography angiography (CCTA) image and determining the blood flow into different regions of the myocardial muscle of the heart into which different branches of the coronary blood vessels lead; and
    simulating a local perfusion of the myocardial muscle for the different regions from the determined blood flow into the different regions of the myocardial muscle of the heart.

14. The method of claim 13, wherein the simulating the local perfusion is based on different loads on a patient.

15. The method of claim 13, further comprising:
    visualizing an image of the myocardial muscle from which the local perfusion for the different regions of the myocardial muscle is identifiable.

16. The method of claim 13, wherein the simulating of the blood flow includes calculating a model of the coronary blood vessels on the basis of the segmented coronary blood vessels and simulating the blood flow with the aid of the model.

17. The method of claim 13, wherein the simulating of the blood flow is done using a lattice Boltzmann method.

18. The method of claim 13, wherein the simulating of the blood flow includes using a statistical model to determine time functions for an arterial inflow and a venous outflow from the imaging data on the basis of an accumulation of a contrast agent in the coronary blood vessels.

19. A non-transitory computer readable medium storing instructions, when executed by a processor, cause the processor to:
    simulate a blood flow through coronary blood vessels on the basis of segmented coronary blood vessels from a static coronary computed tomography angiography (CCTA) image, and determine the blood flow into different regions of the myocardial muscle into which different branches of the coronary blood vessels lead; and
    simulate a local perfusion of the myocardial muscle for the different regions on the basis of the determined blood flow into the different regions of the myocardial muscle.

20. The non-transitory computer readable medium of claim 19, wherein the non-transitory computer readable medium is configured to cause the processor to simulate the local perfusion based on different loads on a patient.

* * * * *